(12) United States Patent
Spindler et al.

(10) Patent No.: US 7,244,860 B2
(45) Date of Patent: Jul. 17, 2007

(54) SUBSTITUTED FERROCENYLDIPHOSPHINES AS LIGANDS FOR HOMOGENEOUS HYROGENERATION CATALYSTS

(75) Inventors: Felix Spindler, Starrkirch-Wil (CH); Matthias Lotz, Basel (CH); Marc Thommen, Nuglar (CH)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 10/556,085

(22) PCT Filed: May 7, 2004

(86) PCT No.: PCT/EP2004/050731

§ 371 (c)(1),
(2), (4) Date: Nov. 9, 2005

(87) PCT Pub. No.: WO2004/099226

PCT Pub. Date: Nov. 18, 2004

(65) Prior Publication Data

US 2006/0241315 A1    Oct. 26, 2006

(30) Foreign Application Priority Data

May 9, 2003    (CH) .................................. 0814/03

(51) Int. Cl.
*C07C 69/63* (2006.01)
(52) U.S. Cl. ...................... 560/231; 556/144; 564/415; 564/422; 554/143; 554/145
(58) Field of Classification Search ................ 560/231; 556/144; 564/415, 422; 554/143, 145
See application file for complete search history.

(56) References Cited

U.S. PATENT DOCUMENTS 6,284,925 B1 * 9/2001 Knochel et al. ............. 564/415
6,348,620 B1 * 2/2002 Knochel et al. ............. 560/231

FOREIGN PATENT DOCUMENTS

EP    0 967 015       12/1999
EP    0 967 015 B1 * 12/1999

OTHER PUBLICATIONS

Hasashi et al., Asymmetric synthesis catalyzed by chiral ferrocenylphosphine-transition metal complexes: VII. New chiral ferrocenylphosphines with C2 symmetry, Journal of Organometallic Chemistry, 1989, 370, pp. 129-139.*

Schwink et al., Enantioselective Preparation of C2 Symmetrical Ferrocenyl Ligands for Asymmetric Catalysis, Chemistry A European Journal, 1998, 4 (5), 950-968.*

Schwink et al., {New C2-symmetrical ferrocenyl diamines as ligands for ruthenium catalyzed transfer hydrogenation, Tetrahedron: Asymmetry, 9, 1998, pp. 1143-1163.*

Christian Markert et al., "Screening of Chiral Catalysts and Catalyst Mixtures by Mass Spectrometric Monitoring of Catalytic Intermediates", Angewandte Chemie, International Edition, 43 (19), pp. 2498-2500, Coden: ACIEF5, ISSN: 1433-7851, XP002293446, 2004.

* cited by examiner

*Primary Examiner*—Thurman Page
*Assistant Examiner*—Chukwuma Nwaonicha
(74) *Attorney, Agent, or Firm*—Wenderoth, Lind & Ponack, L.L.P.

(57) ABSTRACT

Compounds of the formula (I), in which $R_1$ is $C_1$-$C_4$alkyl, $C_6$-$C_{10}$aryl or $C_7$-$C_{11}$, aralkyl, $R_2$ is an open-chain or cyclic secondary amino group, and R is a radical of the formula in which $R_3$ is $C_1$-$C_4$alkyl or $C_1$-$C_4$alkoxy, and $R_4$ is H, $C_1$-$C_4$alkyl or $C_1$-$C_4$alkoxy, are ligands for metal complexes as homogeneous hydrogenation catalysts for prochiral organic compounds containing double bonds, by means of which a very high activity and productivity and also enantioselectivity can be achieved

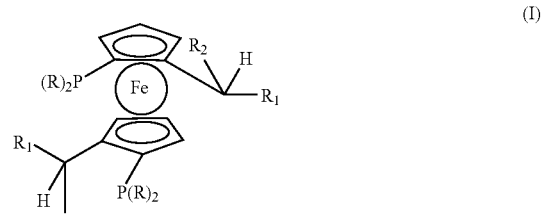

(I)

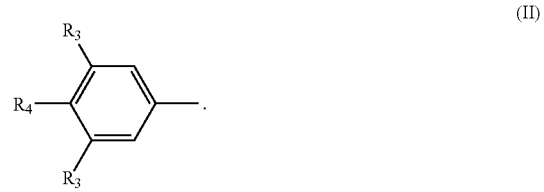

(II)

11 Claims, No Drawings

SUBSTITUTED FERROCENYLDIPHOSPHINES AS LIGANDS FOR HOMOGENEOUS HYROGENERATION CATALYSTS

The present invention relates to 2,2'-bis(α-secondary aminoalkyl)-1,1'-diphosphinoferrocenes having 3,5- or 3,4,5-substituted phenyl radicals in the phosphine groups as ligands for homogeneous hydrogenation catalysts; metal complexes of these ligands with metals of transition group 8 of the Periodic Table of the Elements; and a process for hydrogenating prochiral, ethylenically unsaturated, organic compounds.

EP-A-0 967 015 describes, in quite general terms, 1,1'-diphosphinoferrocenes which are substituted in the 2,2' positions with very different, chiral α-substituted alkyl radicals. Specific mention is made of some 1,1'-diphenylphosphinoferrocenes which are substituted in the 2,2' positions by α-secondary, aminophenylmethyl, for example α-dimethylaminophenylmethyl. These diphosphinoferrocenes act as ligands for effective, homogeneous and enantioselective metal catalysts for the hydrogenation of carbon-carbon or carbon-heteroatom double bonds. No mention is made of a possible influence of substitution of the phenyl radicals in the two phosphino groups.

It has now surprisingly been found that specific substitution of the 3, 5 and possibly 4 positions of the phenyl radicals in the two phosphino groups leads to ligands whose metal complexes display a considerably higher activity and thus also productivity to hydrogenation products and also display a very high enantioselectivity in the hydrogenation of prochiral, ethylenically unsaturated compounds, so that the hydrogenations can even be carried out at atmospheric pressure. Hydrogenation processes using such metal complexes therefore offer significant process engineering and economic advantages.

The invention provides compounds of the formula I in the form of essentially pure enantiomers,

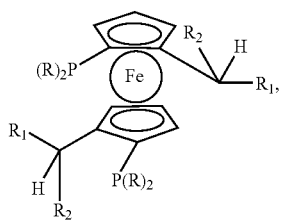
(I)

in which
$R_1$ is $C_1$-$C_4$alkyl, $C_6$-$C_{10}$aryl or $C_7$-$C_{11}$aralkyl,
$R_2$ is an open-chain or cyclic secondary amino group,
and R is a radical of the formula

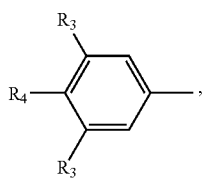

in which
$R_3$ is $C_1$-$C_4$alkyl or $C_1$-$C_4$alkoxy, and
$R_4$ is H, $C_1$-$C_4$alkyl or $C_1$-$C_4$alkoxy.

$C_1$-$C_4$Alkyl radicals $R_1$ can be linear or branched and can be methyl, ethyl, n- or i-propyl and n-, i- or t-butyl. The alkyl is preferably linear. Preferred alkyl radicals $R_1$ are methyl and ethyl.

$C_6$-$C_{10}$Aryl radicals $R_1$ can be, for example, phenyl or naphthyl. A preferred aryl radical $R_1$ is phenyl.

A preferred aralkyl radical $R_1$ is benzyl.

In a preferred embodiment, $R_1$ in the compounds of the formula I is phenyl.

The secondary amino group preferably contains a total of from 2 to 16 carbon atoms, more preferably from 2 to 12 carbon atoms, and particularly preferably from 2 to 6 carbon atoms.

The open-chain or cyclic secondary amino group $R_2$ can correspond to the formula $R_5R_6N-$, where $R_5$ and $R_6$ are each, independently of one another, $C_1$-$C_6$alkyl, preferably $C_1$-$C_4$alkyl, $C_3$-$C_8$cycloalkyl, preferably $C_5$-$C_6$cycloalkyl, $C_6$-$C_{10}$aryl, preferably phenyl, or $C_7$-$C_{11}$aralkyl, preferably benzyl, where the cycloalkyl groups and aryl groups are unsubstituted or substituted by $C_1$-$C_4$alkyl or $C_1$-$C_4$alkoxy, or $R_5$ and $R_6$ together form tetramethylene, pentamethylene or 3-oxapentylene. Examples of alkyl radicals, which are preferably linear, are methyl, ethyl, propyl and butyl. Examples of cycloalkyl radicals are cyclopentyl, cyclohexyl and cyclooctyl.

In a preferred embodiment, $R_5$ and $R_6$ are each methyl, ethyl, phenyl, benzyl, cyclohexyl, or $R_5$ and $R_6$ together form tetramethylene, pentamethylene or 3-oxapentylene. Very particular preference is given to $R_5$ and $R_6$ each being methyl.

Alkyl or alkoxy radicals $R_3$ can be linear or branched and can be methyl, ethyl, n- or i-propyl and n-, i- or t-butyl, or methoxy, ethoxy, n- or i-propoxy and n-, i- or t-butoxy. Preferred alkyl radicals are methyl and t-butyl. Preferred alkoxy radicals are methoxy and t-butoxy.

In a preferred embodiment, both radicals $R_3$ are methyl, t-butyl or methoxy.

Alkyl or alkoxy radicals $R_4$ can be linear or branched. Specific examples have been given for $R_3$.

In a preferred embodiment, $R_4$ is H or methoxy.

Particularly preferred compounds of the formula I are those in which $R_1$ is phenyl, $R_2$ is di-$C_{1-4}$alkylamino, in particular dimethylamino, $R_3$ is methyl, t-butyl or methoxy and $R_4$ is H, methyl or methoxy.

The compounds of the formula I are obtainable by known methods as are described, for example, in EP-A 0 965 574 or by J. J. Almena Perea in Tetrahedron: Asymmetry 10 (1999), pages 375 to 384. The compounds are obtainable, for example, by reacting compounds of the formula II

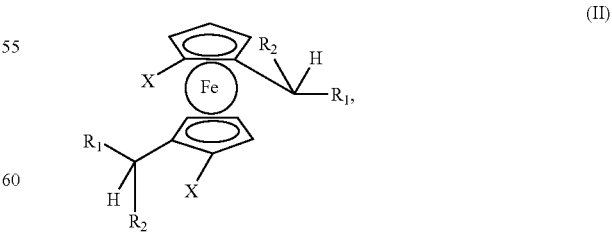
(II)

in which
$R_1$ and $R_2$ have the meanings given for the compounds of the formula I and X is H, Cl, Br or I, preferably H or Br, with an organometallic compound such as lithium alkyl (methyllithium or butyllithium) and subsequently adding a monohalophosphine of the formula III $$X_1-P(R)_2 \quad (III),$$

in which

R is as defined above and $X_1$ is halogen, preferably Cl, Br or I.

The compounds of the formulae II and III are known or can be prepared by analogous methods. The reaction is generally carried out in inert solvents, for example ethers or hydrocarbons. Further details regarding this reaction may be found in the examples. The preparation of substituted halophosphines is known to those skilled in the art and can be carried out either by published preparative methods or by methods analogous to these starting from the appropriately substituted aryl bromides.

The novel compounds of the formula I are ligands for complexes of metals selected from the group of TM8 metals, in particular from the group Ru, Rh and Ir, which are excellent catalysts or catalyst precursors for asymmetric syntheses, for example the asymmetric hydrogenation of prochiral, ethylenically unsaturated, organic compounds. The metal complexes display a very high activity and enantioselectivity. If prochiral unsaturated organic compounds are used, a very high excess of optical isomers can be induced in the synthesis of organic compounds and a high chemical conversion can be achieved in short reaction times. The activity and enantioselectivity for selected substrates is considerably higher than that obtained using known unsubstituted diphosphines. In addition, the productivity can also be increased considerably by means of the metal complexes. In this way, efficient hydrogenation processes can be carried out even at atmospheric pressure.

The invention further provides complexes of metals selected from the group of TM8 metals with compounds of the formula I as ligands.

Possible metals are, for example, Cu, Ag, Au, Ni, Co, Rh, Pd, Ir, Ru and Pt. Preferred metals are rhodium and iridium and also ruthenium, platinum and palladium.

Particularly preferred metals are ruthenium, rhodium and iridium.

Depending on the oxidation number and coordination number of the metal atom, the metal complexes can contain further ligands and/or anions. They can also be cationic metal complexes. Such analogous metal complexes and their preparation are widely described in the literature.

The metal complexes can, for example, correspond to the formulae IV and V, $$A_1MeL_n \quad (IV),$$

$$(A_1MeL_n)^{(z+)}(E^-)_z \quad (V),$$

in which $A_1$ is a compound of the formula I,
the radicals L are identical or different monodentate, anionic or nonionic ligands, or the radicals L are identical or different bidentate, anionic or nonionic ligands;
n is 2, 3 or 4 when L is a monodentate ligand, or n is 1 or 2 when L is a bidentate ligand;
z is 1, 2 or 3;
Me is a metal selected from the group consisting of Rh and Ir; with the metal having the oxidation state 0, 1, 2, 3 or 4;
$E^-$ is the anion of an oxo acid or a complex acid; and
the anionic ligands balance the charge of the oxidation state 1, 2, 3 or 4 of the metal.

The above-described preferences and embodiments apply to the compounds of the formula I.

Monodentate nonionic ligands can, for example, be selected from the group consisting of olefins (for example ethylene, propylene), allyls (allyl, 2-methallyl), solvating solvents (nitriles, linear or cyclic ethers, unalkylated or N-alkylated amides and lactams, amines, phosphines, alcohols, carboxylic esters, sulphonic esters), nitrogen monoxide and carbon monoxide.

Monodentate anionic ligands can, for example, be selected from the group consisting of halide (F, Cl, Br, I), pseudohalide (cyanide, cyanate, isocyanate) and anions of carboxylic acids, sulphonic acids and phosphonic acids (carbonate, formate, acetate, propionate, methylsulphonate, trifluoromethylsulphonate, phenylsulphonate, tosylate).

Bidentate nonionic ligands can, for example, be selected from the group consisting of linear or cyclic diolefins (for example hexadiene, cydooctadiene, norbornadiene), dinitriles (malononitrile), unalkylated or N-alkylated diamides of carboxylic acids, diamines, diphosphines, diols, acetylacetonates, dicarboxylic diesters and disulphonic diesters.

Bidentate anionic ligands can, for example, be selected from the group consisting of anions of dicarboxylic acids, disulphonic acids and diphosphonic acids (for example of oxalic acid, malonic acid, succinic acid, maleic acid, methylenedisulphonic acid and methylene-diphosphonic acid).

Preferred metal complexes also include those in which E is —Cl$^-$, —Br$^-$, —I$^-$, ClO$_4^-$, CF$_3$SO$_3^-$, CH$_3$SO$_3^-$, HSO$_4^-$, BF$_4^-$, B(phenyl)$_4^-$, B(C$_6$F$_5$)$_4^-$, B(3,5-bistrifluoromethylphenyl)$_4^-$, PF$_6^-$, SbCl$_6^-$, AsF$_6^-$ or SbF$_8^-$.

Particularly preferred metal complexes which are suitable for hydrogenations correspond to the formulae VI and VII, $$[A_1Me_1YZ] \quad (VI),$$

$$[A_1Me_1Y]^+E_1^- \quad (VII),$$

in which
$A_1$ is a compound of the formula I;
$Me_1$ is rhodium or iridium;
Y represents two olefins or a diene;
Z is Cl, Br or I; and
$E_1^-$ is the anion of an oxo acid or complex acid.

The above-described embodiments and preferences apply to the compounds of the formula I.

When Y is an olefin, it can be a $C_2$-$C_{12}$-, preferably $C_2$-$C_6$- and particularly preferably $C_2C_4$-olefin. Examples are propene, but-1-ene and in particular ethylene. The diene can contain from 5 to 12, preferably from 5 to 8, carbon atoms and can be an open-chain, cyclic or polycyclic diene. The two olefin groups of the diene are preferably connected by one or two CH$_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably represents two ethylene or 1,5-hexadiene, 1,5-cyclooctadiene or norbornadiene molecules.

In the formula VI, Z is preferably Cl or Br. Examples of $E_1$ are ClO$_4^-$, CF$_3$SO$_3^-$, CH$_3$SO$_3^-$, HSO$_4^-$, BF$_4^-$, B(phenyl)$_4^-$, PF$_6^-$, SbCl$_8^-$, AsF$_8^-$ or SbF$_6^-$.

Ruthenium complexes according to the invention can, for example, correspond to the formula VIII $$[Ru_aH_bZ_c(A_1)_dL_e]_f(E^k)_g(S)_h \quad (VIII),$$

in which
Z is Cl, Br or I; Al is a compound of the formula I; the radicals L are identical or different ligands; $E^-$ is the anion of an oxo acid, mineral acid or complex acid; S is a solvent capable of coordination as ligand; and a is from 1 to 3, b is from 0 to 4, c is from 0 to 6, d is from 1 to 3, e is from 0 to 4, f is from 1 to 3, g is from 1 to 4, h is from 0 to 6 and k is from 1 to 4, with the net charge on the complex being zero.

The above-described preferences for Z, $A_1$, L and $E^-$ apply to the compounds of the formula VIII. The ligands L can additionally be arenes or heteroarenes (for example benzene, naphthalene, methylbenzene, xylene, cumene, 1,3, 5-mesitylene, pyridine, biphenyl, pyrrole, benzimidazole or cyclopentadienyl) and metal salts having a Lewis acid function (for example $ZnCl_2$, $AlCl_3$, $TiCl_4$ and $SnCl_4$). The solvent ligands can be, for example, alcohols, amines, acid amides, lactams and sulphones.

Complexes of this type are described in the references mentioned below and the references cited therein:

D. J. Ager, S. A. Laneman, Tetrahedron: Asymmetry, 8, 1997, 3327-3355;

T. Ohkuma, R. Noyori in Comprehensive Asymmetric Catalysis (E. N. Jacobsen, A. Pfaltz, H. Yamamoto, Eds.), Springer, Berlin, 1999, 199-246;

J. M. Brown in Comprehensive Asymmetic Catalysis (E. N. Jacobsen, A. Pfaltz, H. Yamamoto, Eds.), Springer, Berlin, 1999, 122-182;

T. Ohkuma, M. Kitamura, R. Noyori in Catalytic Asymmetric Synthesis, 2nd Edition (I. Ojima, Ed.), Wiley-VCH New York, 2000, 1-110;

N. Zanetti, et al. Organometallics 15, 1996, 860.

More specific ruthenium complexes having corresponding formulae but other diphosphine ligands are described in the following references:

[$Ru_aH_bCl_c(A_1)_d$arene$_e$](amine)$_h$: EP-A1-0 269 395 and EP-A1-0 174 057;

[$Ru_a(A_1)$]$E^-$, more specifically [$Ru(A_1)$]$E^-$ and [$RuH(A_1)$]$E^-$: EP-A1-0 256 634;

[$Ru(A_1)$(carboxylate)$_2$]: U.S. Pat. No. 4,739,084 and AP-A1-0 245 959;

[$Ru(A_1)_2$(Lewis acid)]($NC_2H_5$)$_3$, [$Ru(A_1)_2$(Lewis acid)(acetate): EP-A1-0 307 168;

[$RuZ$(arene)($A_1$)]halide, [$Ru(Z)$(arene)($A_1$)]$E^-$: EP-A1-0 366 390;

[$RuZ_2(A_1)$] (chiral amine): H. Doucet et al., Angew. Chem. Int. Ed. 37, 1998, 1703; T. Ohkuma, et al., J. Am. Chem. Soc., 120, 1998 13529; T. Ohkuma, et al., J. Am. Chem. Soc., 122, 2000, 6510.

[$RuZ_2(A_1)$] (pyridine)$_2$: O. M. Akotsi et al., Chirality, 12 (2000) 514.

Some specific and preferred ruthenium complexes are: [Ru(acetate)$_2(A_1)$], [Ru(OOCCF$_3$)$_2(A_1)$], [RuCl$_2(A_1)$], [RuBr$_2(A_1)$], [RuI$_2(A_1)$], [Ru$_2$Cl$_4(A_1)_2$](Nethyl$_3$), [Ru$_3$Cl$_4A_1)_2$](Nethyl$_3$)(xylene), [RuCl(benzene)($A_1$)]Cl, [RuBr(benzene)($A_1$)]Br, [RuI(benzene)($A_1$)]I, [RuCl(p-cumene)($A_1$)]Cl, [RuBr(p-cumene)($A_1$)]Br, [RuI(p-cumene)($A_1$)]I, [Ru(2-methallyl)$_2(A_1)$], [RuCl$_2$(phenyl-CN)$_2(A_1)$], [Ru($A_1$)(AcO)$_2$(ethanol)$_2$], [(Cp)Ru($A_1$)]Cl, [(Cp)Ru($A_1$)]PF$_6$, [RuCl(Pphenyl$_3$)-($A_1$)]$_2$(η-Cl)$_2$, [RuCl$_2$($A_1$)(dpen)] and [RuCl$_2(A_1)$(daipen)]. Cp is cyclopentadienyl; dpen and daipen are each a chiral ethylenediamine, for example 1,2-diphenylethylene-1,2-diamine or 1,1-di(p-methoxyphenyl)-2-isopropylethylene-1,2-diamine.

The metal complexes of the invention are prepared by methods known from the literature (cf. U.S. Pat. No. 5,371,256, U.S. Pat. No. 5,446,844, U.S. Pat. No. 5,583,241 and E. Jacobsen, A. Pfaltz, H. Yamamoto (Eds.), Comprehensive Asymmetric Catalysis I to III, Springer Verlag, Berlin, 1999, and references cited therein).

The metal complexes of the invention are homogeneous catalysts, or catalyst precursors which can be activated under the reaction conditions, which can be used for the asymmetric hydrogenation of prochiral, ethylenically unsaturated, organic compounds. Such hydrogenations using soluble homogeneous metal complexes are described, for example, in Pure and Appl. Chem., Vol. 68, No. 1, pp. 131-138 (1996). According to the invention, preference is given to using complexes of ruthenium, rhodium and iridium for the hydrogenation. Particularly good results are achieved in the hydrogenation of prochiral compounds having a carbon double bond. The high activity also enables the amount of catalyst to be reduced, which offers economic advantages.

The invention further provides for the use of complexes of metals selected from the group of TM8 metals with ligands including compounds of the formula I as homogeneous catalysts for the asymmetric hydrogenation of prochiral, ethylenically unsaturated, organic compounds by means of hydrogen.

A further aspect of the invention is a process for preparing chiral organic compounds by asymmetric hydrogenation of prochiral, organic compounds containing at least one carbon double bond by means of hydrogen in the presence of a homogeneous catalyst, wherein the addition reaction is carried out in the presence of catalytic amounts of at least one complex of metals selected from the group of TM8 metals with compounds of the formula I as ligands.

Preferred prochiral, unsaturated compounds to be hydrogenated can contain one or more, identical or different groups C=C in open-chain or cyclic organic compounds, where the groups C=C can be part of a ring system or be exocyclic groups. The prochiral unsaturated compounds can be alkenes, cycloalkenes, heterocycloalkenes. They can, for example, correspond to the formula IX, $$R_5R_6C=CR_7R_8 \quad (IX),$$

in which $R_5$, $R_6$, $R_7$ and $R_8$ are selected so that the compound is prochiral and are each, independently of one another, hydrogen or an open-chain or cyclic hydrocarbon radical or heterohydrocarbon radical containing heteroatoms selected from the group consisting of O, S and N, which contain from 1 to 30, preferably from 1 to 20, carbon atoms;

$R_5$ and $R_6$ together with the carbon atom to which they are bound form a hydrocarbon ring or heterohydrocarbon ring having from 3 to 12 ring atoms;

$R_5$ and $R_7$, in each case together with the C=C group to which they are bound, form a hydrocarbon ring or heterohydrocarbon ring having from 3 to 12 ring atoms;

the heteroatoms in the heterocyclic rings are selected from the group consisting of O, S and N;

and $R_5$, $R_6$, $R_7$ and $R_8$ are unsubstituted or substituted by $C_1$-$C_6$alkyl, $C_1$-$C_6$alkoxy, cyclohexyl, $C_6$-$C_1$aryl, $C_7$-$C_{12}$aralkyl, $C_1$-$C_4$alkyl-$C_6$-$C_{10}$aryl, $C_1$-$C_4$alkoxy-$C_6$-$C_{10}$aryl, $C_1$-$C_4$alkyl-$C_7$-$C_{12}$aralkyl, $C_1$-$C_4$alkoxy-$C_7$-$C_{12}$aralkyl, —OH, —$NR_{11}R_{12}$, —CO—$OR_9$ or —CO—$NR_{10}R_{11}$, where $R_9$ is H, an alkali metal, $C_1$-$C_6$alkyl, cyclohexyl, phenyl or benzyl and $R_{10}$ and $R_{11}$ are each, independently of one another, hydrogen, $C_1$-$C_6$alkyl, cyclohexyl, phenyl or benzyl, or $R_{10}$ and $R_{11}$ together form a tetramethylene, pentamethylene or 3-oxapenlylene group.

Examples of and preferences for substituents have been mentioned above.

Radicals $R_5$ to $R_7$ can, for example, be $C_1$-$C_{20}$alkyl, preferably $C_1$-$C_{12}$alkyl, $C_1$-$C_{20}$heteroalkyl, preferably $C_1$-$C_{12}$heteroalkyl, containing heteroatoms selected from the group consisting of O, S and N, $C_3$-$C_{12}$cycloalkyl, preferably $C_4$-$C_8$cycloalkyl, C-bonded $C_3$-$C_{11}$heterocycloalkyl, preferably $C_4$-$C_8$heterocycloalkyl, containing heteroatoms selected from the group consisting of O, S and N, $C_3$-$C_{12}$cycloalkyl-$C_1$-$C_6$alkyl, preferably $C_4$-$C_8$Cycloalkyl-$C_1$-$C_6$alkyl, $C_3$-$C_{11}$heterocycloalkyl-$C_1$-$C_6$alkyl, preferably $C_4$-$C_8$-heterocycloalkyl-$C_1$-$C_6$alkyl, containing heteroatoms selected from the group consisting of O, S and N, $C_6$-$C_{14}$aryl, preferably $C_6$-$C_{10}$aryl, $C_5$-$C_{13}$heteroaryl, preferably $C_5C_9$heteroaryl, containing heteroatoms selected from the group consisting of O, S and N, $C_7$-$C_{15}$aralkyl, preferably $C_7$-$C_{11}$aralkyl, $C_6$-$C_{12}$heteroaralkyl, preferably $C_6$-$C_{10}$heteroaralkyl, containing heteroatoms selected from the group consisting of O, S and N.

When $R_5$ and $_6$ or $R_5$ and $R_7$, in each case together with the group to which they are bound, form a hydrocarbon ring or heterohydrocarbon ring, the ring preferably contains from 4 to 8 ring atoms. The heterohydrocarbon ring can, for example, contain from 1 to 3, preferably one or two, heteroatoms.

Some examples of unsaturated organic compounds are unsaturated carboxylic adds and dicarboxylic acids, esters, amides and salts, for example α- and possibly β-substituted acrylic acids or crotonic acids. Preferred carboxylic acids are those of the formula

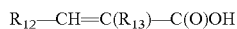

$R_{12}$—CH=C($R_{13}$)—C(O)OH and also their salts, esters and amides, in which $R_{12}$ is $C_1$-$C_6$alkyl, unsubstituted $C_3$-$C_8$cycloalkyl or $C_3$-$C_8$cycloalkyl substituted by from 1 to 4 $C_1$-$C_6$alkyl, $C_1$-$C_6$alkoxy or $C_1$-$C_6$alkoxy-$C_1$-$C_4$alkoxy groups, or unsubstituted $C_8$-$C_{10}$aryl or $C_6$-$C_{10}$aryl substituted by from 1 to 4 $C_1$-$C_8$alkyl, $C_1$-$C_8$alkoxy, $C_1$-$C_6$alkoxy-$C_1$-$C_4$alkoxy groups, preferably phenyl, and $R_{13}$ is linear or branched $C_1$-$C_6$alkyl (for example isopropyl), unsubstituted or substituted (in the manner defined above) cyclopentyl, cyclohexyl, phenyl or protected amino (for example acetylamino). Further specific classes of substrates for the hydrogenation are, for example, prochiral allyl alcohols and α- or β-enamides.

The process of the invention can be carried out at low or elevated temperatures, for example temperatures in the range from −20 to 150° C., preferably from −10 to 100° C., particularly preferably from 10 to 80° C. The optical yields are generally better at lower temperatures than at higher temperatures.

The process of the invention can be carried out at atmospheric pressure or super-atmospheric pressure. The pressure can be, for example, from $10^4$ to $2\times10^7$ Pa (pascal), preferably from $10^5$ to $2\times10^6$ Pa and particularly preferably in the range from atmospheric pressure to $10^6$ Pa.

Catalysts are preferably used in amounts of from 0.00001 to 10 mol %, particularly preferably from 0.0001 to 10 mol %, and in particular from 0.001 to 5 mol %, based on the compound to be hydrogenated. The molar ratio of compound to be hydrogenated to homogeneous catalyst can be, for example, from 10 to 10 000 000 and more preferably from 20 to 100 000.

The preparation of the catalysts and hydrogenations and addition reactions can be carried out in the presence or absence of an inert solvent, with it being possible to use one solvent or mixtures of solvents. Suitable solvents are, for example, allphatic, cycloaliphatic and aromatic hydrocarbons (pentane, hexane, heptane, petroleum ether, cyclohexane, methylcyclohexane, benzene, toluene, xylene), aliphatic halogenated hydrocarbons (methylene chloride, chloroform, dichloroethane and tetrachloroethane), nitrites (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboxamides (dimethylacetamide, dimethylformamide), acyclic ureas (dimethylimidazoline) and sulphoxides and sulphones (dimethyl sulphoxide, dimethyl sulphone, tetramethylene sulphoxide, tetramethylene sulphone) and alcohols (methanol, ethanol, propanol, butanol, ethylene glycol monomethyl ether, ethylene glycol monoethyl ether, diethylene glycol monomethyl ether), nitromethane and water.

The reactions can be carried out in the presence of cocatalysts, for example quaternary ammonium halides (tetrabutylammonium iodide) and/or in the presence of protic adds, for example mineral adds (cf., for example. U.S. Pat. No. 5,371,256, U.S. Pat. No. 5,446,844 and U.S. Pat. No. 5,583,241 and EP-A-0 691 949). The cocatalysts are particularly useful for hydrogenations.

The metal complexes used as catalysts can be added as separately prepared, isolated compounds or can be formed in situ prior to the reaction and then mixed with the substate to be hydrogenated. It can be advantageous to additionally add ligands in the reaction using isolated metal complexes, or to use an excess of the ligands in the in-situ preparation. The excess can be, for example, from 1 to 30 mol %, preferably from 1 to 10 mol %, based on the metal compound used for the preparation. In the in-situ preparation of the catalysts, it is also possible to use salts of the diphosphine ligands, for example halides or tetrafluoroborates The process of the invention is generally carried out by initially placing the catalyst in the reaction vessel and then adding the substrate or vice versa, if appropriate reaction auxiliaries and then hydrogen, and then starting the reaction. The hydrogen is preferably introduced under pressure. The process can be carried out continuously or batchwise in various types of reactor.

The chiral organic compounds which can be prepared according to the invention are active substances or intermediates for the preparation of such substances, in particular in the field of preparation of pharmaceuticals and agrochemicals.

The following examples illustrate the invention.

A) PREPARATION OF DIPHOSPHINES

Example A1

Preparation of (αR, αR)-2,2'-bis(α-N,N-dimethylaminophenylmethyl)-(S,S)-1,1'-bis[di(3,5-dimethyl-4-methoxyphenyl)phosphino]ferrocene (R,R)-1,1'-Bis(α-N,N-dimethylaminophenylmethyl)ferrocene is prepared as described in the literature: a) J. J. Almena Perea, A. Börner, P. Knochel, *Tetrahedron Lett.* 1998, 39 (44), 8073-8076; b) J. J. Almena Perea, M. Lotz, P. Knochel, *Tetrahedron: Asymmetry* 1999, 10 (2), 375-384; c) L. Schwink, P. Knochel, *Tetrahedron Lett.* 1996, 37 (1), 25-28. d) L. Schwink, P. Knochel, *Chem. Eur. J.,* 1998, 4 (5), 950-968.).

t-BuylLi(4.42 ml, 6.63 mmol, 3.0 equivalents; 1.5 M in pentane) is added dropwise at 0° C. under argon to a solution of (R,R)-1,1'-bis(α-N,N-dimethylaminophenylmethyl)ferrocene (1.00 g, 2.21 mmol) in dry tertbutyl methyl ether (TBME) (20 ml) over a period of 5 minutes. The solution obtained is stirred for 1 hour at 0° C. Chlorobis(3,5-dimethyl-4-methoxyphenyl)-phosphine (2.61 g, 7.74 mmol, 3.5 equivalents) is subsequently added over a period of 5 minutes and the reaction mixture is stirred at room temperature for 1 hour. The mixture is poured into saturated NaHCO$_3$ solution (100 ml), the organic phase is separated off and the aqueous phase is extracted with TBME (3×100 ml). The combined organic phases are washed with saturated NaCl solution (100 ml), dried over Na$_2$SO$_4$, filtered and the solvent is removed on a rotary evaporator. The crude product is dissolved in CH$_2$Cl$_2$ and purified by column chromatography (250 g of silica gel, n-heptane/TBME 2:1); R$_f$ (n-heptane/TBME 2:1): 0.11). The resulting yellow solid (1.10 g) is suspended in methanol (5 ml) and refluxed for 15 minutes. After cooling to room temperature, the suspension is filtered and the solid obtained in this way is dried. The title compound (0.73 g, 0.69 mmol, 31% of theory) is obtained in the form of a yellow solid. $^{31}$P-NMR (C$_6$D$_6$): −22.7 ppm (s); optical rotation [a]$_D^{20}$: −61.5° (C=1.0, CHCl$_3$).

Example A2

Preparation of (αR,αR)-2,2'-bis(α-N,N-dimethylaminophenylmethyl)-(S,S)-1,1'-bis[di(3,5-dimethylphenyl)phosphino]ferrocene 20 g (44.2 mmol) of (R,R)-1,1'-bis(α-N,N-dimethylaminophenylmethyl)ferrocene together with 160 ml of TBME are placed in a reaction vessel at 0° C. under argon. 88.4 ml of t-butylLi (1.5 M in pentane, 132.6 mmol) are then added dropwise at 0-3° C. over a period of 40 minutes. The reaction solution is stirred for another 2 hours at 0° C. 42.82 g (154.7 mmol) of bis(3,5-dimethylphenyl)chlorophosphine suspended in 100 ml of TBME are subsequently added dropwise at 3-7° C. The reaction solution is firstly stirred for 2 hours at 0° C. and then overnight at room temperature.

The solution is then hydrolyzed at 0° C. by means of 250 ml of saturated, aqueous sodium hydrogencarbonate solution and the mixture is extracted with TBME. The organic phases are washed with saturated sodium chloride solution, combined, dried over sodium sulphate, filtered and then evaporated to dryness.

This gives 62 g of crude product. Chromatography two times over silica gel 60 using hexane/ethyl acetate 19:1 (then changed to hexane/ethyl acetate 9:1) gives 12.9 g (44.2 mmol; 31%) of the title compound. Recrystallization from diethyl ether/pentane gives 6.56 g (7.03 mmol; 15.9%) of analytically pure (αR,αR)-2,2'-bis(α-N,N-dimetlhylaminophenylmethyl)-(S,S)-1,1'-bis[di(3,5-dimethylphenyl)phosphino]ferrocene.

B) USE EXAMPLES

Example B1

Preparation of Methyl N-acetylphenylalanine 4.7 mg (0.0126 mmol) of [Rh(norbornadiene)$_2$]BF$_4$ and 13.9 mg (0.0132 mmol) of the compound from Example A1 are placed under argon in a flask provided with a magnetic stirrer by repeated evacuation and flushing. After addition of 5 ml of degassed methanol, the solution is stirred for 15 minutes. 2.77 g (0.01265 mol) of cis-methyl acetamidocinnamate and 5 ml of degassed methanol are subsequently introduced into a 10 ml Schlenk flask in which an argon atmosphere prevails and stirred for 15 minutes. The ratio of substrate/catalyst is 1000. The catalyst solution and the substrate solution are injected in succession by means of a steel capillary into a 100 ml glass reactor filled with argon. Finally, 1.05 bar of hydrogen are introduced in 4 flushing cycles (argon/hydrogen). The glass reactor is heated to 25° C. and the hydrogenation is started by switching on the stirrer. The course of the reaction can be followed via the hydrogen consumption (pressure drop in the hydrogen reservoir). After a reaction time of 2 hours, conversion and enantiomeric purity of the product are measured (by means of GC: column Chirasil-L-Val 50 m). The conversion is 100%, and the enantioselectivity (ee) is 98.7% (R).

Comparison for Example B1

The procedure of Example B1 is repeated, but the ligand (αR,αR)-2,2'-bis(α-N,N-dimethylaminophenylmethyl)-(S,S)-1,1'-bis(diphenylphosphino)ferrocene (10.8 mg, 0.0132 mmol) is used. The reaction is complete only after 4 hours. The conversion is 100%, and the enantiomeric purity of methyl N-acetylphenylalanine (ee) is 97.6% (R).

Example B2

Preparation of Methyl N-acetylphenylalanine

This is carried out by a method analogous to Example B1. 6.9 g (31.48 mmol) of cis-methyl acetamidocinnamate, 1.2 mg (0.0032 mmol) of [Rh(norbornadiene)$_2$]OBF$_4$, 3.7 mg (0.0035 mmol) of the compound from Example A1 and a total of 40 ml of methanol are used. The ratio of substrate/catalyst is 10 000. The reaction temperature is 35° C., and the hydrogen pressure is 1.05 bar. After 1.3 hours, the reaction is stopped. The conversion is 100%, and the enantiomeric purity (ee) of methyl N-acetylphenylalanine is 98.6% (R).

Example B3

Preparation of Methyl N-acetylphenylalanine

This is carried out by a method analogous to Example B1. 13.8 g (63.01 mmol) of cis-methyl acetamidocinnamate, 1.2 mg (0.0032 mmol) of [Rh(norbornadiene)$_2$]BF$_4$, 3.7 mg (0.0035 mmol) of the compound from Example A1 and a total of 80 ml of methanol are used. The ratio of substrate/catalyst is 19 640. The reaction temperature is 25° C., and the hydrogen pressure is 1.05 bar. After 7 hours, the reaction is stopped. The conversion is 100%, and the enantiomeric purity of methyl N-acetylphenylalanine (ee) is 98.6% (R).

Example B4

Preparation of 2-Methylbutyric Acid 6.2 mg (0.0063 mmol) of [RuI$_2$(cumene)]$_2$ and 14.0 mg (0.0133 mmol) of (αR,αR)-2,2'-bis(α-N,N-dimethylaminophenylmethyl)-(S,S)-1,1'-bis[di(3,5-dimethyl-4-methoxyphenyl)phosphino]-ferrocene from Example A1 are placed under argon in a flask provided with a magnetic stirrer by repeated evacuation and flushing. After addition of 5 ml of degassed methanol, the solution is stirred for 15 minutes. 0.253 g (2.53 mol) of tiglic acid and 5 ml of degassed methanol are subsequently introduced into a 10 ml Schlenk flask in which an argon atmosphere prevails and stirred for 15 minutes. The ratio of substrate/catalyst is 200. The catalyst solution and the substrate solution are injected in succession by means of a steel capillary into a 50 ml autoclave filled with argon. Finally, 1.05 bar of hydrogen are introduced in 4 flushing cycles (argon/hydrogen). The autoclave is heated to 25° C. and the hydrogenation is started by switching on the stirrer. The course of the reaction can be followed via the hydrogen consumption (pressure drop in the hydrogen reservoir). After a reaction time of 18 hours, conversion and enantiomeric purity of the product are measured (by means of GC: column Betadex 110, 30 m). The conversion is 100%, and the enantioselectivity (ee) is 97.2%.

Example B5

Preparation of Methyl N-acetylphenylalanine

The procedure of Example B1 is repeated using 555 mg (2.53 mmol) of methyl acetamidocinnamate. The ratio of substrate/catalyst is 100. (αR,αR)-2,2'-Bis(α-N,N-dimethylaminophenylmethyl)-(S,S)-1,1'-bis[di(3,5-dimethylphenyl)phosphino]ferrocene from Example A2 is used as ligand. 100% conversion after 1 hour; ee=98.7%.

What is claimed is:

1. A compound of the formula I in the form of essentially pure enantiomers,

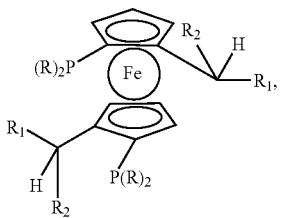

(I)

in which $R_1$ is $C_1$-$C_4$alkyl, $C_6$-$C_{10}$aryl or $C_7$-$C_{11}$aralkyl, $R_2$ is an open-chain or cyclic secondary amino group, and R is a radical of the formula

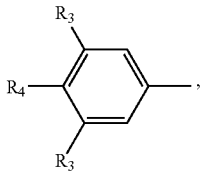

in which $R_3$ is $C_1$-$C_4$alkyl or $C_1$-$C_4$alkoxy, and $R_4$ is H, $C_1$-$C_4$alkyl or $C_1$-$C_4$alkoxy.

2. A compound according to claim 1, wherein $R_1$ is phenyl in the compounds of the formula I.

3. A compound according to claim 1, wherein the open-chain secondary amino group $R_2$ corresponds to the formula $R_5R_6N$—, where $R_5$ and $R_6$ are each, independently of one another, $C_1$-$C_6$alkyl, $C_3$-$C_8$cycloalkyl, $C_6$-$C_{10}$aryl, or $C_7$-$C_{11}$aralkyl, where the cycloalkyl groups and aryl groups are unsubstituted or substituted by $C_1$-$C_4$alkyl or $C_1$-$C_4$alkoxy, or $R_5$ and $R_6$ together form tetramethylene, pentamethylene or 3-oxapentylene.

4. A compound according to claim 3, wherein $R_5$ and $R_6$ are each methyl.

5. A compound according to claim 1, wherein both radicals $R_3$ are methyl, t-butyl or methoxy.

6. A compound according to claim 1, wherein $R_4$ is H or methoxy.

7. A compound according to claim 1, wherein, in compounds of the formula I, $R_1$ is phenyl, $R_2$ is di-$C_1$-$C_4$alkylamino, $R_3$ is methyl, t-butyl or methoxy and $R_4$ is H, methyl or methoxy.

8. A complex of a metal selected from the group consisting of metals of transition group 8 of the Periodic Table of the Elements with compounds of the formula I according to claim 1 as ligands.

9. A metal complex according to claim 8, wherein the metal is rhodium, iridium or ruthenium.

10. A process for preparing chiral organic compounds by asymmetric hydrogenation of prochiral, organic compounds containing at least one carbon double bond by means of hydrogen in the presence of a homogeneous catalyst, wherein the hydrogenation is carried out in the presence of catalytic amounts of at least one complex of a metal selected from the group consisting of metals of transition group 8 of the Periodic Table of the Elements with compounds of the formula I according to claim 1 as ligands.

11. A compound according to claim 7, wherein $R_2$ is dimethylamino.

* * * * *